US008992387B2

(12) United States Patent
Watterson et al.

(10) Patent No.: US 8,992,387 B2
(45) Date of Patent: Mar. 31, 2015

(54) INDOOR-OUTDOOR EXERCISE SYSTEM

(71) Applicant: ICON Health & Fitness, Inc., Logan, UT (US)

(72) Inventors: Scott R. Watterson, Logan, UT (US); Mark Watterson, Logan, UT (US)

(73) Assignee: ICON Health & Fitness, Inc., Logan, UT (US)

(*) Notice: Subject to any disclaimer, the term of this patent is extended or adjusted under 35 U.S.C. 154(b) by 119 days.

(21) Appl. No.: 13/752,153

(22) Filed: Jan. 28, 2013

(65) Prior Publication Data

US 2013/0210580 A1  Aug. 15, 2013

Related U.S. Application Data

(60) Provisional application No. 61/597,720, filed on Feb. 11, 2012.

(51) Int. Cl.
*G06F 19/00* (2011.01)
*A63B 24/00* (2006.01)

(52) U.S. Cl.
CPC ............ *G06F 19/3481* (2013.01); *A63B 24/00* (2013.01)
USPC .......................................................... 482/8

(58) Field of Classification Search
CPC ........... A63B 2225/20; A63B 2225/50; A63B 24/0062
USPC ............................ 482/1–9, 900–902; 434/247
See application file for complete search history.

(56) References Cited

U.S. PATENT DOCUMENTS

| 6,152,856 | A | 11/2000 | Studor et al. | |
|---|---|---|---|---|
| 6,447,424 | B1 | 9/2002 | Ashby et al. | |
| 6,450,922 | B1 | 9/2002 | Henderson et al. | |
| 6,749,537 | B1 | 6/2004 | Hickman | |
| 6,902,513 | B1 * | 6/2005 | McClure | 482/8 |
| 6,921,351 | B1 | 7/2005 | Hickman et al. | |
| 7,549,947 | B2 | 6/2009 | Hickman et al. | |
| 7,637,847 | B1 | 12/2009 | Hickman | |
| 7,645,212 | B2 | 1/2010 | Ashby et al. | |
| 7,670,263 | B2 | 3/2010 | Ellis | |
| 7,857,731 | B2 | 12/2010 | Hickman et al. | |
| 8,029,415 | B2 | 10/2011 | Ashby et al. | |
| 8,033,959 | B2 * | 10/2011 | Oleson et al. | 482/9 |
| 8,152,695 | B2 * | 4/2012 | Riley et al. | 482/9 |

(Continued)

FOREIGN PATENT DOCUMENTS

| KR | 10-2010-0020337 | 2/2010 |
|---|---|---|
| WO | 98-50121 | 11/1998 |

OTHER PUBLICATIONS

International Search Report, PCT/US2013/023557, May 15, 2013.

*Primary Examiner* — Glenn Richman
(74) *Attorney, Agent, or Firm* — Workman Nydegger

(57) ABSTRACT

An embodiment of an exercise system includes an exercise monitoring device that gathers data regarding an outdoor exercise routine. Additionally, a remote communication system communicatively connectable to the exercise monitoring device is receptive to the data regarding the outdoor exercise routine such that the remote communication system generates an exercise program based on the data regarding the outdoor exercise routine. Furthermore, an exercise device that is communicatively connectable to the remote communication system may receive the exercise program and simulate one or more aspects of the outdoor exercise routine.

17 Claims, 6 Drawing Sheets

(56) References Cited

U.S. PATENT DOCUMENTS

| | | | |
|---|---|---|---|
| 8,506,457 B2* | 8/2013 | Baudhuin | 482/57 |
| 8,715,139 B2* | 5/2014 | DiBenedetto et al. | 482/9 |
| 2004/0117214 A1* | 6/2004 | Shea | 705/2 |
| 2009/0023554 A1 | 1/2009 | Shim | |
| 2010/0056340 A1* | 3/2010 | Ellis et al. | 482/4 |
| 2010/0062818 A1 | 3/2010 | Haughay et al. | |
| 2011/0143887 A1 | 6/2011 | Choi | |
| 2011/0164044 A1 | 7/2011 | Huang | |
| 2013/0210579 A1 | 8/2013 | Schieffer et al. | |
| 2013/0210581 A1 | 8/2013 | Watterson et al. | |
| 2013/0210582 A1 | 8/2013 | Del Toro et al. | |
| 2014/0056437 A1* | 2/2014 | DiBenedetto et al. | 381/77 |

* cited by examiner

INDOOR-OUTDOOR EXERCISE SYSTEM

RELATED APPLICATIONS

This application claims the benefit under 35 U.S.C. §119(e) of U.S. Provisional Patent Application No. 61/597,720 filed Feb. 11, 2012 titled "Indoor-Outdoor Exercise System." The provisional application is incorporated herein by reference in its entirety.

TECHNICAL FIELD

This disclosure relates generally to systems, methods, and devices for exercise. More particularly, the disclosure relates to an exercise system that allows a user to take an indoor exercise experience outdoors and an outdoor exercise experience indoors.

BACKGROUND

More people are becoming aware of the need to exercise in order to maintain or improve their health and fitness. Accordingly, increasing numbers of people can be found exercising outdoors (e.g., walking, running, biking) and indoors (e.g., on treadmills, stationary bikes, ellipticals). There are advantages and drawbacks to exercising outdoors. Similarly, there are advantages and drawbacks to exercising indoors. For instance, exercising outdoors provides a person with varied scenery and terrain. However, a person's schedule, inclement weather, and other factors may prohibit the person from exercising outdoors. In such circumstances, the person may find it more convenient to exercise indoors. Unfortunately, some people find that frequently exercising indoors can become monotonous due to the lack of variation in scenery and terrain.

In an attempt to make exercising indoors more enjoyable, various exercise devices and systems have been developed to more closely simulate exercising outdoors. For instance, U.S. Pat. No. 6,450,922 discloses an exercise system that includes a route computer mounted on a bicycle. When a user rides the bicycle outdoors, the route computer collects data about the ridden route. When the user desires to ride indoors, the bicycle and route computer can be connected to a base controller and a resistance unit. The base controller can use the data collected by the route computer to adjust the resistance provided by the resistance unit and thereby simulate the previously ridden outdoor route.

Other exercise devices and systems that simulate outdoor exercise experiences are disclosed in U.S. Pat. No. 6,447,424, U.S. Pat. No. 6,749,537, U.S. Pat. No. 6,921,351, U.S. Pat. No. 7,549,947, U.S. Pat. No. 7,637,847, U.S. Pat. No. 7,645,212, U.S. Pat. No. 8,029,415, and U.S. Pat. No. 7,857,731.

SUMMARY OF THE INVENTION

In one aspect of the disclosure, an exercise system includes an exercise monitoring device that gathers data regarding an outdoor exercise routine.

In one or more other aspects that may be combined with any of the aspects herein, an exercise system includes a remote communication system that is communicatively connectable to an exercise monitoring device.

In one or more other aspects that may be combined with any of the aspects herein, a remote communication system is receptive to data regarding an outdoor exercise routine.

In one or more other aspects that may be combined with any of the aspects herein, a remote communication system generates an exercise program based on data regarding an outdoor exercise routine.

In one or more other aspects that may be combined with any of the aspects herein, an exercise system includes an exercise device that is communicatively connectable to a remote communication system.

In one or more other aspects that may be combined with any of the aspects herein, an exercise device is receptive to an exercise program.

In one or more other aspects that may be combined with any of the aspects herein, an exercise program causes an exercise device to simulate one or more aspects of an outdoor exercise routine.

In one or more other aspects that may be combined with any of the aspects herein, an exercise monitoring device comprises one or more sensors that gather data about an outdoor exercise routine, including at least one of Global Positioning System (GPS) data, distance traveled, elevation, elevation changes, time duration, incline, and decline.

In one or more other aspects that may be combined with any of the aspects herein, an exercise monitoring device comprises at least one of a display and a speaker.

In one or more other aspects that may be combined with any of the aspects herein, a remote communication system generates an exercise program by creating one or more control commands that cause adjustments to one or more operating parameters of an exercise device.

In one or more other aspects that may be combined with any of the aspects herein, adjustments to one or more exercise device operating parameters simulate one or more aspects of an outdoor exercise routine.

In one or more other aspects that may be combined with any of the aspects herein, one or more simulated aspects of an outdoor exercise routine include at least one of incline, decline, and speed.

In one or more other aspects that may be combined with any of the aspects herein, a remote communication system generates an exercise program by synchronizing one or more images of an outdoor exercise routine with one or more control commands.

In one or more other aspects that may be combined with any of the aspects herein, simulation of one or more aspects of an outdoor exercise routine comprises presenting one or more images of the outdoor exercise routine on a display of an exercise device.

In one or more other aspects that may be combined with any of the aspects herein, an exercise system includes a remote communication system that generates exercise programs based on data regarding outdoor exercise routes.

In one or more other aspects that may be combined with any of the aspects herein, an exercise system includes an exercise device that generates exercise programs based on data regarding outdoor exercise routes.

In one or more other aspects that may be combined with any of the aspects herein, exercise programs include (i) control commands representative of terrain of outdoor exercise routes and (ii) images of the outdoor exercise routes that are synchronized with the control commands.

In one or more other aspects that may be combined with any of the aspects herein, an exercise device is communicatively connected to a remote communication system.

In one or more other aspects that may be combined with any of the aspects herein, an exercise device is receptive to exercise programs, wherein the exercise device simulates outdoor exercise routes in response to the exercise programs.

In one or more other aspects that may be combined with any of the aspects herein, data regarding an exerciser's performance of a simulated exercise route is gathered during the performance of the simulated exercise route.

In one or more other aspects that may be combined with any of the aspects herein, an exercise monitoring device gathers data regarding an exerciser's performance of an exercise performed along an outdoor exercise route and compares that data to data regarding the exerciser's performance of a simulated route.

In one or more other aspects that may be combined with any of the aspects herein, an exercise monitoring device provides prompts to the exerciser while the exerciser performs an exercise along an outdoor exercise route.

In one or more other aspects that may be combined with any of the aspects herein, prompts inform an exercise about the exerciser's performance along an outdoor exercise route in comparison to the exerciser's performance of a simulated exercise route.

DETAILED DESCRIPTION

Figure 1:
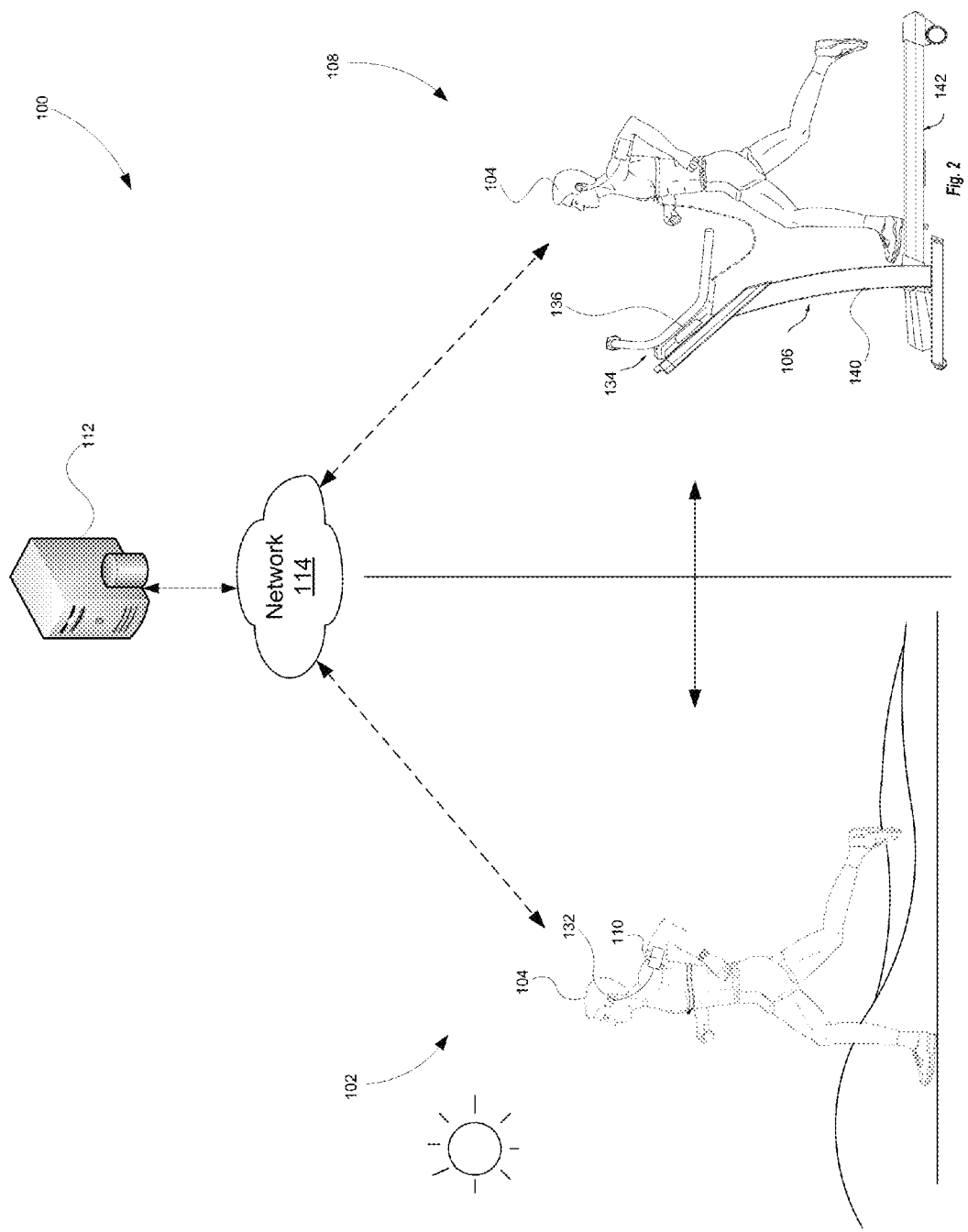
FIG. 1 illustrates an exercise system according to one exemplary embodiment.

The present disclosure is directed to systems, methods, and devices for exercise. More specifically, the present disclosure is related to an exercise system 100, and related devices and methods that enable an exerciser to take an outdoor exercise experience indoors and an indoor exercise experience outdoors. For instance, as shown in FIG. 1 generally at 102, exercise system 100 according to one embodiment of the invention may enable an exerciser 104 to exercise outdoors during an outdoor exercise session. Exercise system 100 may monitor various aspects of the outdoor exercise session and then allow for the outdoor exercise session to be simulated or experienced indoors (e.g., on an exercise device 106), as shown generally at 108. Likewise, exercise system 100 may enable the exerciser 104 to exercise indoors (e.g., on exercise device 106) during an exercise session, as shown at 108. Exercise system 100 may monitor various aspects of the indoor exercise session and then allow for the indoor session to be simulated or experienced outdoors, as shown at 102.

As shown in FIG. 1, exercise system 100 includes an exercise monitoring device 110 that may be worn or carried by exerciser 104. Optionally, one or both of exercise monitoring device 110 and exercise device 106 may be communicatively connectable to one another and/or a remote communication system 112 (e.g., a website or server). Although not illustrated, one or both of exercise monitoring device 110 and exercise device 106 may optionally be communicatively connectable to one or more computers, which in turn are communicatively connectable to remote communication system 112. Communication with remote communication system 112 may be facilitated or made through a network 114. Network 114 may be a wide area network, such as the Internet, or a local area network.

Figure 2:
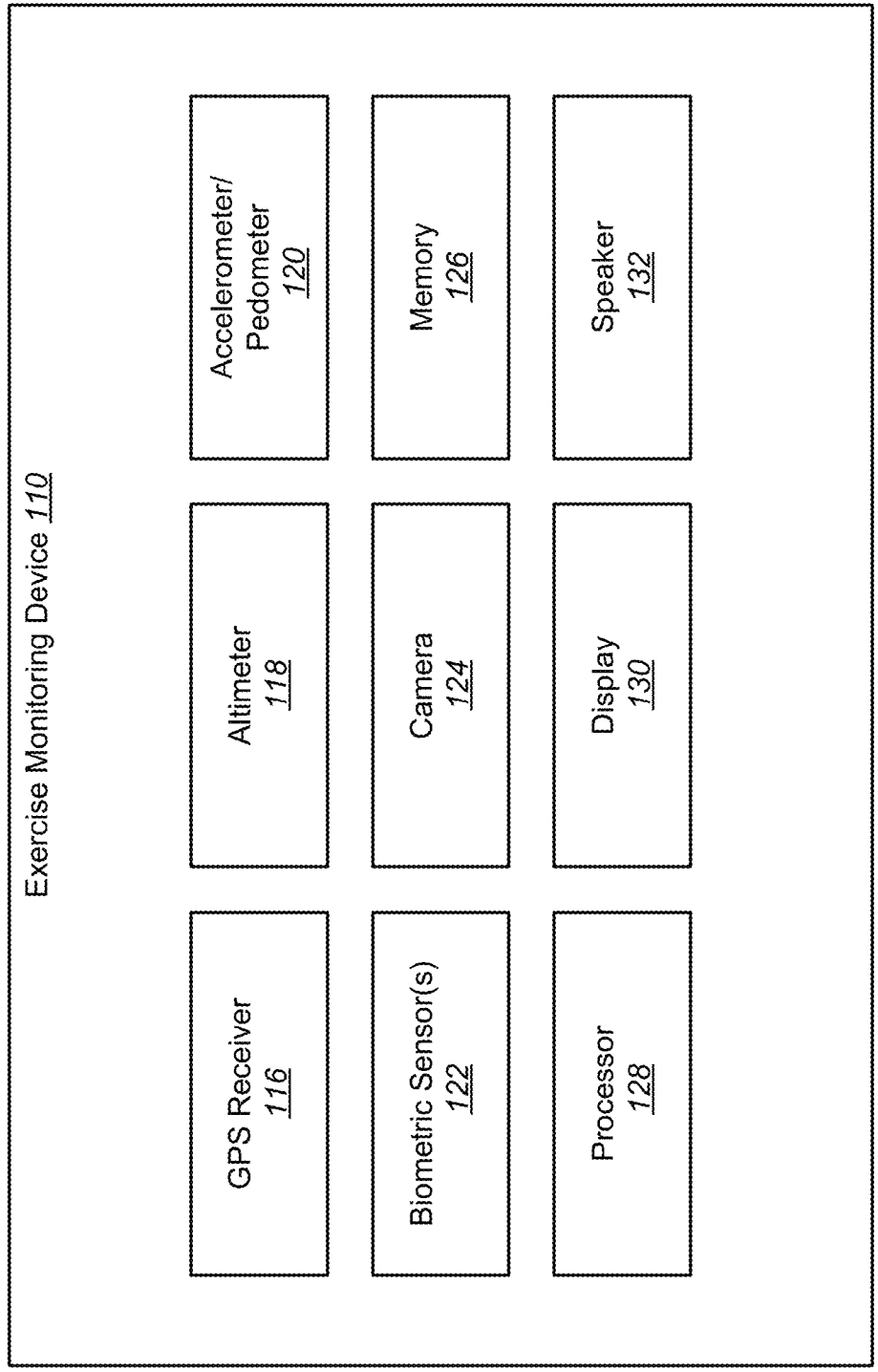
FIG. 2 is a block diagram of an exercise monitoring device for use in connection with the exercise system of FIG. 1.

Exercise monitoring device 110 may include various sensors, hardware, and software components. As shown in FIG. 2, for example, exercise monitoring device 110 may include one or more components for gathering exercise related information. Such components may include a GPS receiver 116 that tracks the position and movements of exerciser 104 during an outdoor exercise session. Another gathering component may include an altimeter 118 that tracks an exerciser's current elevation (whether indoors or outdoors) and/or changes in elevation during an outdoor exercise session. Exercise monitoring device 110 may also include an accelerometer/pedometer 120 to track information such as an exerciser's footfalls, cadence, speed, and the like. One or more biometric sensors 122 may also be included to track physiological conditions of exerciser 104 (e.g., heart rate, calories burned, temperature, perspiration). Still further, exercise monitoring device 110 may include a camera 124 that gathers images (still or moving) of the exerciser's outdoor route.

While FIG. 2 suggests that all of the components of exercise monitoring device 110 are part of a single unit or contained within a single housing, this is only exemplary. Some or all of the components of exercise monitoring device 110 may, alternatively, be separate from, yet connectable to one another. For instance, as shown in FIG. 1, speaker 132 is illustrated as an earphone that is connected to other components of exercise monitoring device 110. The connections between the various components of exercise monitoring device 110 may be various types of connections. For instance, one or more of the components may be connected together, directed or indirectly, so that the components are held together in fixed relation to one another (e.g., within the same housing). Alternatively, or additionally, the components may be communicatively connected to one another. Such communicative connections may be wired or wireless connections.

The information collected by the gathering components of exercise monitoring device 110 can be stored in a memory 126 and, optionally, processed by a processor 128. During or after an exercise session, whether indoors or outdoors, the exercise related information gathered by exercise monitoring device 110 can be uploaded to remote communication system 112 and/or exercise device 106. Additionally, exercise monitoring device 110 may also include one or more presentation components for presenting the exercise related information to exerciser 104. For instance, exercise monitoring device 110 may include a display 130 and/or a speaker 132 for visually and/or audibly presenting the exercise related information to exerciser 104.

Figure 3:
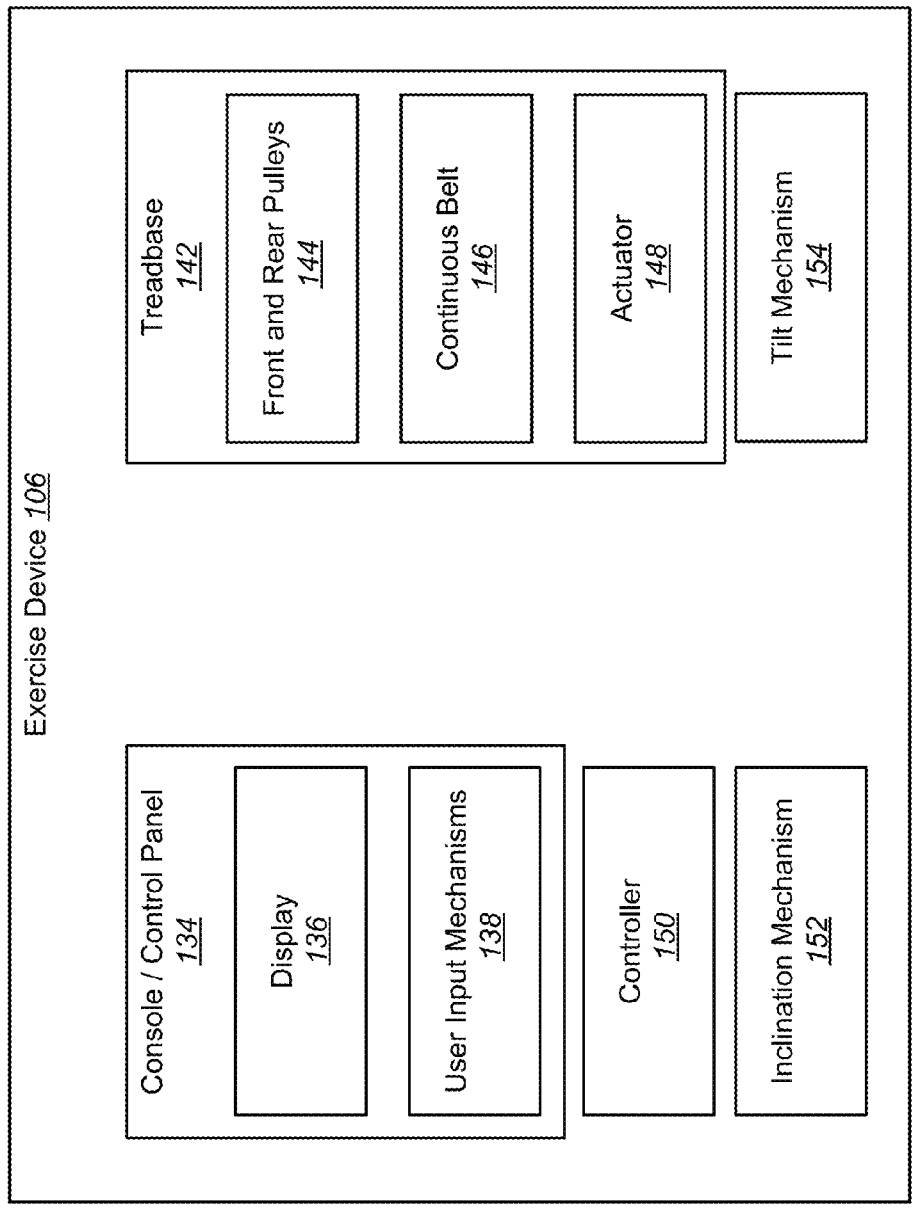
FIG. 3 is block diagram of the exercise device for use in connection with the exercise system of FIG. 1.

In the illustrated embodiment, as shown in FIG. 1 and the block diagram of FIG. 3, exercise device 106 is depicted as a treadmill and includes a console or control panel 134 having a display 136 and user input mechanisms 138 that may be used to control various aspects of exercise device 106. Control panel 134 is illustrated as being supported on a generally upright support structure 140. A treadbase 142 is connected to support structure 140 and typically includes front and rear pulleys 144 with a continuous belt 146 extending between and around front and rear pulleys 144. Treadbase 142, front and rear pulleys 144, and continuous belt 146 may be considered, individually or collectively, as movable elements that are movable during the performance of an exercise.

As is common with electric treadmills, at least one of front and rear pulleys 144 may be mechanically connected to an actuator 148, such as an electric belt drive motor. In the illustrated embodiment, belt drive motor 148 turns either front or rear pulley 144 in order to rotate continuous belt 146. Belt drive motor 148 is electrically connected to a controller 150 that controls the operation of belt drive motor 148, and thus the speed of the continuous belt 146, in response to various inputs. The speed of continuous belt 146 is one example of an adjustable operating parameter of exercise device 106.

Controller 150 may take the form of a computer, a processor, a microprocessor, a microcontroller, state machine or other similar device that includes circuitry for controlling the operation of one or more features on exercise device 106, including the operating parameter(s) of the movable element(s), as is further detailed in FIG. 6 below. Controller 150 may also perform other functions, such as receiving and implementing control commands received from remote communication system 112 and/or exercise monitoring device 110.

In addition to the ability to control and vary the speed of continuous belt 146, exercise device 106 may also permit the degree of incline of treadbase 142 to be varied. For instance, treadbase 142 can be oriented in a neutral position, an inclined position, or a declined position. In the neutral position, treadbase 142 may be generally parallel to a support surface, as shown in FIG. 1. In the inclined position, the front portion of treadbase 142 (e.g., the end of treadbase 142 adjacent to support structure 140) is vertically higher than the rear portion of treadbase 142 to enable an exerciser to simulate walking or running up a hill. Similarly, in a declined position the front portion of treadbase 142 is vertically lower than the rear portion of treadbase 142 to enable an exerciser to simulate walking or running down a hill.

The inclining and declining capabilities of treadbase 142 provide exercise device 106 with additional operating parameters that may be adjusted to vary the intensity of exercises performed on exercise device 106 or to simulate real world terrain. The inclination and declination of treadbase 142 can be accomplished through the use of an incline mechanism 152. One example incline mechanism includes an extension mechanism connected between support structure 140 and treadbase 142. The extension mechanism can include an incline motor that may be controlled by controller 150 to cause an extension member of the extension mechanism to extend or retract in order to move treadbase 142 between the declined, neutral, and inclined positions.

The side-to-side tilt of treadbase 142 may also be varied to simulate for an exerciser the experience of walking or running on uneven ground. For instance, treadbase 142 can be tilted to the left so that the left side of treadbase 142 is vertically lower than the right side of treadbase 142. Similarly, treadbase 142 can be tilted to the right so that the right side of treadbase 142 is vertically lower than the left side of treadbase 142.

The side-to-side tilting of treadbase 142 can be accomplished through the use of tilt mechanism 154. One example tilt mechanism includes an extension mechanism connected between support structure 140 and treadbase 142. The extension mechanism can include a tilt motor that may be controlled by controller 150 to cause an extension member of the tilt mechanism to extend or retract in order to raise or lower one side of treadbase 142 relative to the other side of treadbase 142.

While the block diagram of FIG. 3 illustrates some of the components of exercise device 106 being grouped together and other components being separate, this is exemplary only. For instance, belt drive motor 148 is shown as part of treadbase 142. However, belt drive motor 148 may be separate from treadbase 142. By way of example, belt drive motor 148 may be mounted on support structure 140. Similarly, while not so illustrated in FIG. 3, controller 150 may be incorporated into console or control panel 134 or treadbase 142.

Figure 4:
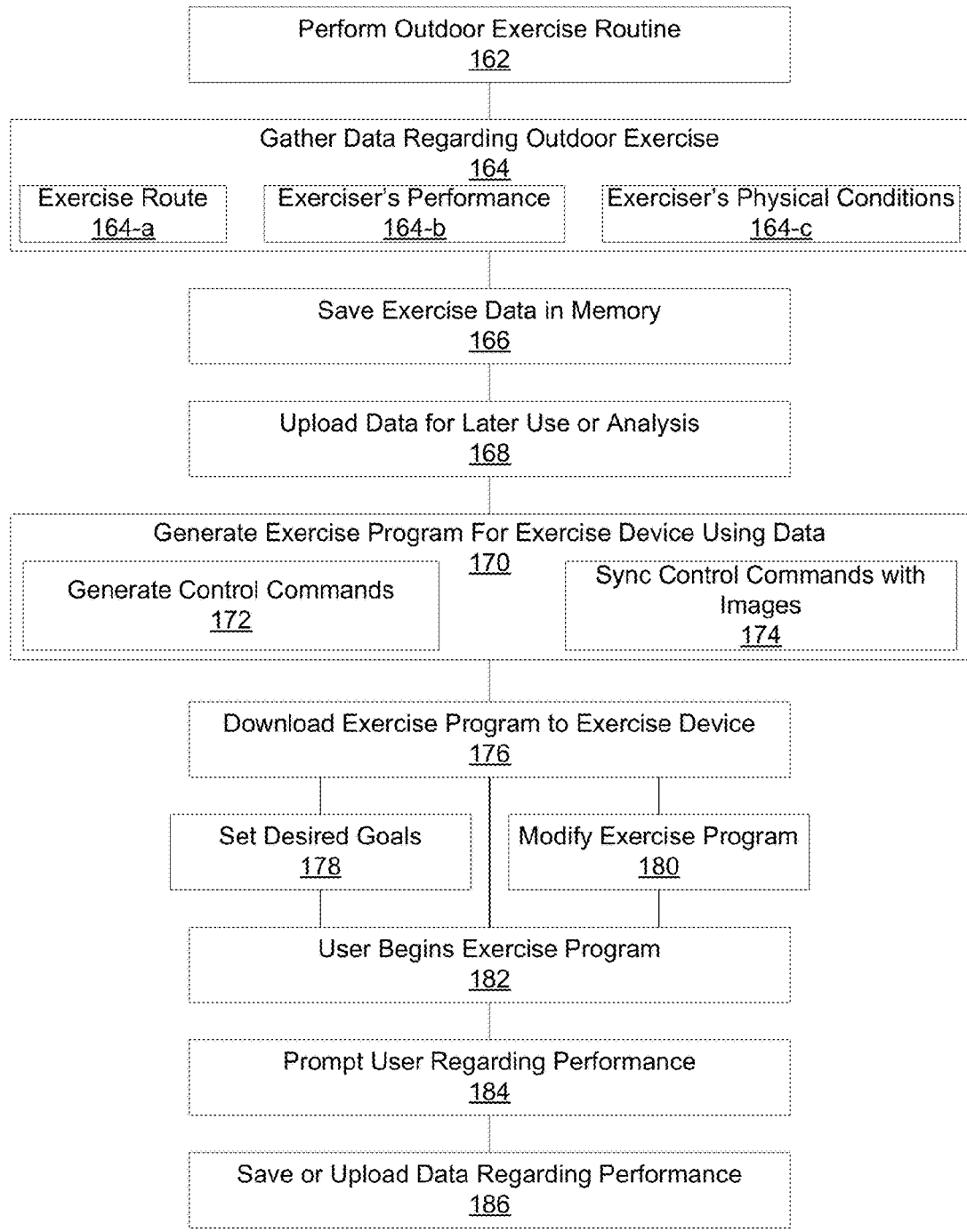
FIG. 4 is a functional block diagram of a process for taking an outdoor exercise experience indoors using the exercise system of FIG. 1.
Figure 5:
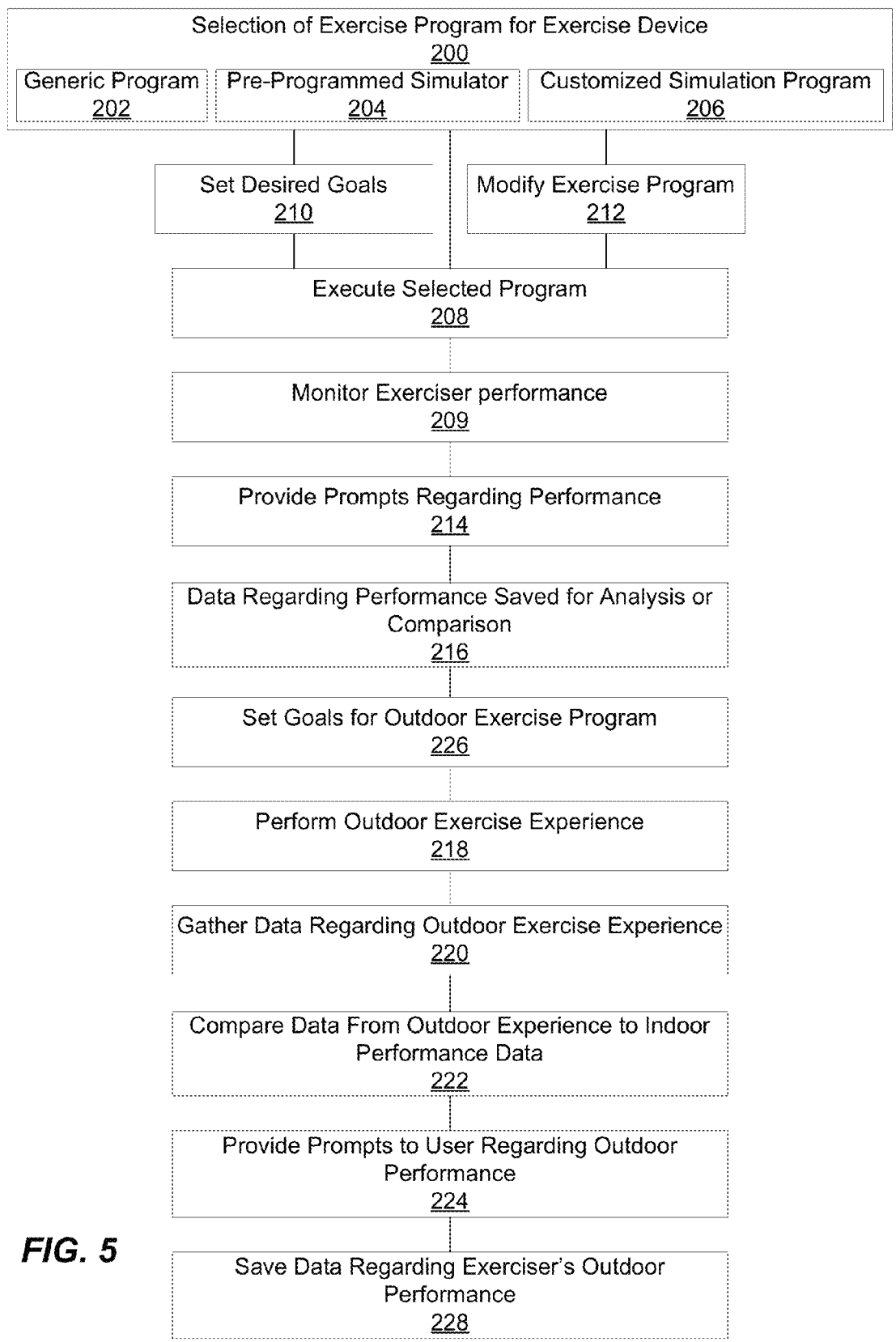
FIG. 5 is a functional block diagram of a process for taking an indoor exercise experience outdoors using the exercise system of FIG. 1.

Attention is now directed to FIGS. 4-5, which depict flow chart diagrams related to the use and operation of exercise system 100. More specifically, FIG. 4 relates to the use and operation of exercise system 100 as it relates to taking an outdoor exercise experience indoors. In contrast, FIG. 5 relates to the use and operation of exercise system 100 as it relates to taking an indoor exercise experience outdoors.

With attention to FIG. 4, a flow diagram depicts an exemplary process 160 for taking an outdoor exercise experience indoors. According to the illustrated embodiment, the process starts at 162 by performing an outdoor exercise routine. The outdoor exercise routine may be, for example, going for a walk, jog, run, bike ride, or the like outdoors.

While performing the outdoor exercise routine, data regarding the outdoor exercise routine is gathered, as indicated at 164. The gathering of the data may be performed by exercise monitoring device 110 and may relate to one or more categories of data (e.g., the exercise route 164A, the exerciser's performance 164B, the exerciser's physiological conditions 164C, and the like). By way of example, the data related to the exercise route may include GPS data related to the course traveled, images (still or moving) of the course traveled, the distance traveled, the start time/stop time/duration of the outdoor exercise routine, elevation changes, weather conditions, and the like. Similarly, the data related to the exerciser's performance may include the exerciser's speed, cadence, pace, and the like. The data related to the exerciser's physiological condition may include the exerciser's heart rate, calories burned, perspiration, temperature, and the like.

As shown at 166, the data gathered regarding the outdoor exercise routine may be saved, for example in memory 126 of exercise monitoring device 110. During or after the completion of the outdoor exercise routine, the gathered data may be uploaded (at 168) for later use or analysis. For instance, the data may be uploaded to remote communication system 112 via a wireless/cellular network. Alternatively, after completion of the outdoor exercise routine, exercise monitoring device 110 may be docketed with or connected to a computer or exercise device 106 to upload the data to the computer or exercise device 106. Optionally, the computer or exercise device 106 may in turn upload the data to remote communication system 112.

As indicated at 170, the data about the outdoor exercise routine may then be used to generate an exercise program for use with exercise device 106. The exercise program may be generated by exercise monitoring device 110, remote communication system 112, exercise device 106, or a separate computer. Execution of the exercise program may cause exercise device 106 to simulate the outdoor exercise routine by adjusting the operating parameters of exercise device 106 so as to mimic various aspects of the outdoor exercise routine (e.g., terrain). Generation of the exercise program includes generating one or more control commands (172). When executed, the control commands cause the operating parameters of exercise device 106 to be adjusted. More specifically, the control commands cause the actuators of exercise device 106 to adjust, which results in adjustment of the operating parameters. For instance, a control command may cause incline mechanism 152 to extend, thereby increasing the incline of treadbase 142.

In addition to generating control commands, generation of the exercise program may optionally include synchronizing the control commands with the gathered images of the course or route traveled during the outdoor exercise routine, as indicated at 174. Synchronization of the images and control commands can include associating each image with one or more control commands that cause exercise device 106 to simulate the outdoor exercise routine at the location where the image was taken.

Depending on where the exercise program is generated, the exercise program may then be downloaded or streamed to exercise device 106, as indicated at 176. For instance, if the exercise program is generated by remote communication system 112, the exercise program may be downloaded or streamed to exercise device 106 through network 114. However, if the exercise program is generated at exercise device 106, step 176 can be omitted.

Once the exercise program is available to exercise device 106, the exercise program can be run or executed, as indicated at 182. As suggested above, running or executing the exercise program causes exercise device 106 to simulate the outdoor exercise routine by adjusting the operating parameters of exercise device 106 to replicate the outdoor exercise routine (e.g., the terrain, difficulty level, speed). In addition, running the exercise program can display on display 136 and/or display 130 the gathered images from the outdoor exercise routine.

Prior to running the exercise program on exercise device 106, and as indicated at 178, the exerciser may set various goals related to how he/she would like to perform during the exercise program. For instance, the exerciser may desire to complete the simulated routine in the same amount of time or in less time than it took to complete to actual outdoor exercise routine. Similarly, the exerciser may set goals related to his/her desired pace, cadence, speed, heart rate, and the like. The exerciser can enter his/her goals into exercise device 106 via user input mechanisms 138. In addition to setting desired goals, the exerciser may also modify the exercise program prior to running the exercise program, as indicated at 180. For instance, the exerciser may set maximum incline, decline, tilt, or speed values for the simulated route.

While the exerciser is performing the exercise program on exercise device 106, exercise system 100 may monitor the exerciser's performance and provide the exerciser with prompts regarding his/her performance, as indicated at 184. The prompts may inform the exerciser about how his/her current performance compared to his/her performance during the actual outdoor exercise routine. For instance, the prompts may indicate how far ahead or behind schedule he/she is compared to his/her time during the actual outdoor exercise routine. Similarly, the prompt may inform the exerciser how he/she is performing compared to his/her goals. The prompts may be presented to the exerciser via one or more of displays 130, 136, speaker 132, or a speaker on exercise device 106.

As indicated at 186, during or after the exerciser's performance of the exercise program on exercise device 106, data regarding the exerciser's performance can be saved and/or uploaded to exercise monitoring device 110 and/or remote communication system 112. The data can be stored for later analysis and/or to comparison to later exercise routines. Such analysis and/or comparison may be used to determine whether the exerciser's performance is improving from one exercise session to another or whether the exerciser performs better indoors or outdoors. Once such determinations are made, the data may be used to improve the exerciser's performance in the weaker venue or in future exercise sessions.

Attention is now directed to FIG. 5, which depicts a flow diagram of an exemplary process for taking an indoor exercise experience outdoors. According to the illustrated embodiment, the process starts at 200 with the selection of an exercise program to be run on exercise device 106. Exercise programs available for selection may include generic exercise programs (202), preprogrammed simulation programs (204), and customized simulation programs (206).

The generic exercise programs may include the type of exercise programs commonly found on exercise devices, such as "hill" or interval programs. The programs may include control commands that periodically vary the incline and/or speed of the movable elements.

The preprogrammed simulation programs may simulate real world routes. That is, the preprogrammed simulation programs may include one or more control commands that simulate the terrain (e.g., inclines, declines) or other characteristics of a route in the real world. The preprogrammed simulation programs may also include display programming that depicts the real world route. The control commands and the display programming of the preprogrammed simulation programs may be synchronized so that the exercise device simulates the terrain depicted by the display programming. The preprogrammed simulation programs may come preloaded on exercise device 106. Alternatively, or additionally, the preprogrammed simulation programs may be downloaded or streamed to exercise device 106 from remote communication system 112 and/or exercise monitoring device 110.

Like the preprogrammed simulation programs, the customized simulation programs may simulate real world routes via control commands and/or display programming. Unlike the preprogrammed simulation programs, the customized simulation programs may be at least partially defined by the user. The exerciser may select or define a desired real world route that he/she would like to run. For instance, the user may select or define the route of an upcoming race (e.g., a city marathon) that the exerciser would like to train for. The exerciser may select or define the desired route via user input mechanisms 138, a user input on exercise monitoring device 110, or a separate computer.

The selected or defined route may be communicated to remote communication system 112. Remote communication system 112 may use the selected route to create an exercise program that simulates the selected route. In particular, remote communication system 112 may create control commands that will cause exercise device 106 to simulate the terrain and/or other characteristics of the selected route. Additionally, remote communication system 112 may also synchronize images of the selected route with the control commands. Once created, the customized simulation program may be downloaded or streamed to exercise device 106. It is understood, however, that the customized simulation program may be created by exercise device 106, exercise monitoring device 110, or a separate computer.

In any case, once the exercise program has been selected, the selected exercise program can be run or executed, as indicated at 208. Running or executing the selected exercise program causes exercise device 106 to adjust its operating parameters. In the case of a generic exercise program, the control commands periodically cause changes in the operating parameters. In the case of a simulation program, whether preprogrammed or customized, the control commands cause the exercise device 106 to simulate the real world route that is the subject of the simulation program. If the simulation program includes display programming related to the real world route, the display programming may also be displayed when the simulation program is run.

Prior to running the exercise program on exercise device 106, and as indicated at 210, the exerciser may set various goals related to how he/she would like to perform during the performance of the exercise program. For instance, the exerciser may desire to complete the simulation program in a certain amount of time. Similarly, the exerciser may set goals related to his/her desired pace, cadence, speed, heart rate, and the like. The exerciser can enter his/her goals into exercise device 106 via user input mechanisms 138. In addition to setting desired goals, the exerciser may also modify the exercise program prior to running the exercise program, as indicated at 212. For instance, the exerciser may set maximum distance, incline, decline, tilt, or speed values for the simulated route.

While the exerciser is performing the exercise program on exercise device 106, exercise system 100 may monitor the exerciser's performance (at 209) and provide the exerciser with prompts regarding his/her performance, as indicated at 214. The prompts may inform the exerciser about how his/her current performance compared to his/her performance goals. For instance, the prompts may indicate how far ahead or behind schedule he/she is compared to his/her goals. The prompts may be presented to the exerciser via one or more of displays 130, 136, speaker 132, or a speaker on exercise device 106.

As indicated at 216, during or after the exerciser's performance of the exercise program on exercise device 106, data regarding the exerciser's performance can be saved for later analysis and/or to comparison to later exercise routines. For instance, the data may be saved at exercise device 106. The data may also be sent to and saved at remote communication system 112 and/or exercise monitoring device 110.

Once the data regarding the exerciser's performance on exercise device 106 of the exercise program is stored at remote communication system 112 or exercise monitoring device 110, the exerciser can take the indoor exercise experience outdoors by performing an outdoor exercise experience, as indicated at 218. For instance, if the exercise program run on exercise device 106 was a simulation program that simulated a real world route, the exerciser could actually run the real world route. As the exerciser runs the actual real world route, exercise monitoring device 110 can gather data regarding the exerciser's performance, as indicated at 220. The gathered data may be compared (at either exercise monitoring device 110 or remote communication system 112) to the exerciser's indoor performance data (209), as indicated at 222.

Based on the comparison between the user's performances, exercise system 100 may provide the exerciser with prompts regarding his/her performance, as indicated at 224. The prompts may inform the exerciser about how his/her current performance compared to his/her performance during the simulated (i.e., indoor) exercise routine. For instance, the prompts may indicate how far ahead or behind schedule he/she is compared to his/her time during the simulated exercise routine. The prompts may be presented to the exerciser via display 130 and/or speaker 132.

Prior to running the actual real world route, and as indicated at 226, the exerciser may set various goals related to how he/she would like to perform during the outdoor exercise routine. For instance, the exerciser may desire to complete the actual real world route in a certain amount of time. Similarly, the exerciser may set goals related to his/her desired pace, cadence, speed, heart rate, and the like. The exerciser can enter his/her goals into exercise monitoring device 110.

As indicated at 228, during or after the exerciser's performance of the outdoor exercise routine, data regarding the exerciser's performance can be saved for later analysis and/or to comparison to later exercise routines. For instance, the data may be saved at exercise monitoring device 110. The data may also be sent to remote communication system 112 and/or exercise device 106.

Figure 6:
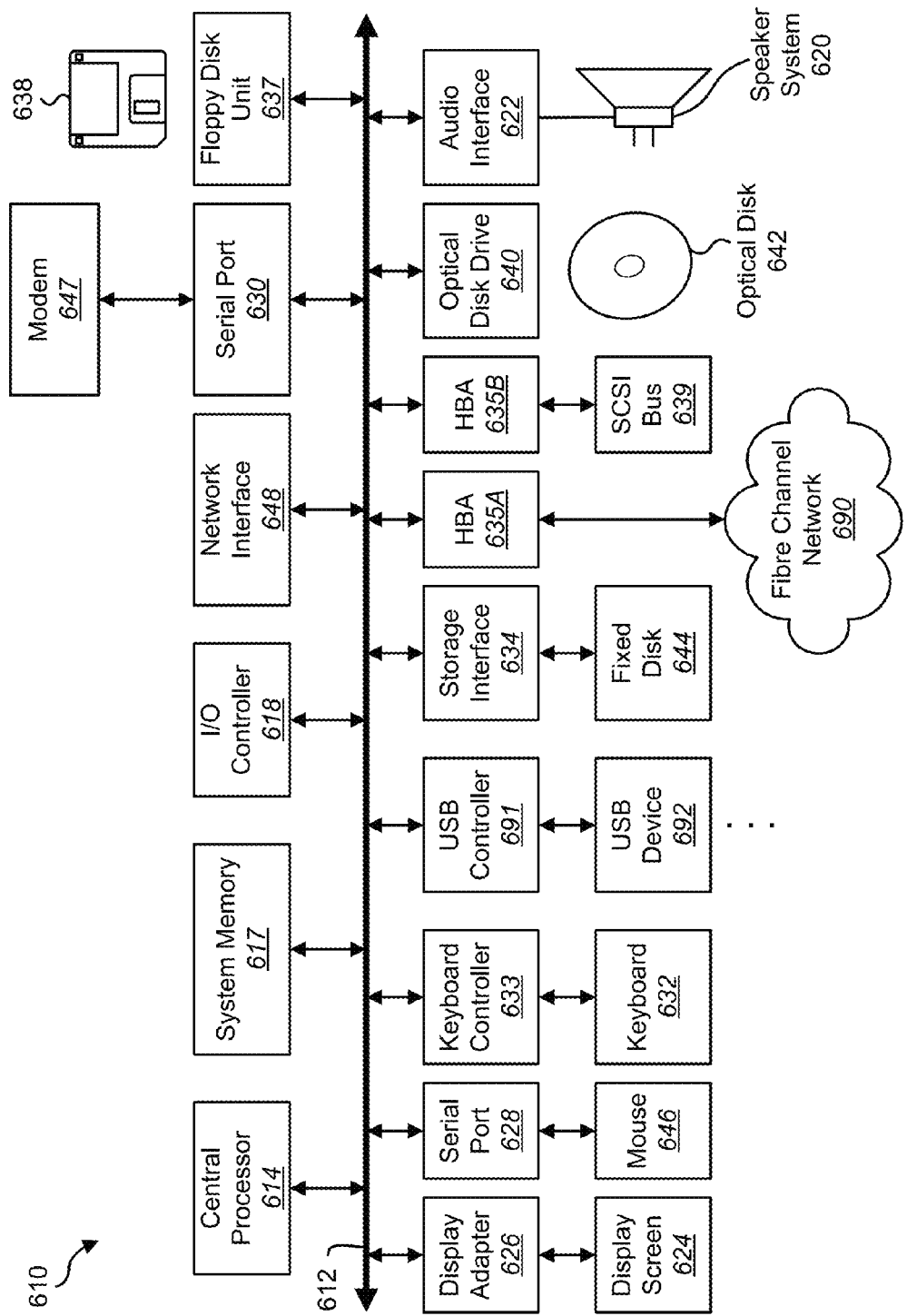
FIG. 6 depicts a block diagram of a computer system suitable for implementing the present systems and methods.

FIG. 6 depicts a block diagram of a computer system 610 suitable for implementing the present systems and methods. The computer system 610 may be a primary or an alternative example of the exercise monitoring device 110, the remote communications system 112, the console or control panel 134, and/or the controller 150 of FIG. 1, 2, or 3. Computer system 610 includes a bus 612 which interconnects major subsystems of computer system 610, such as a central processor 614, a system memory 617 (typically RAM, but which may also include ROM, flash RAM, or the like), an input/output controller 618, an external audio device, such as a speaker system 620 via an audio output interface 622, an external device, such as a display screen 624 via display adapter 626, serial ports 628 and 630, a keyboard 632 (interfaced with a keyboard controller 633), multiple USB devices 692 (interfaced with a USB controller 691), a storage interface 634, a floppy disk unit 637 operative to receive a floppy disk 638, a host bus adapter (HBA) interface card 635A operative to connect with a Fibre Channel network 690, a host bus adapter (HBA) interface card 635B operative to connect to a SCSI bus 639, and an optical disk drive 640 operative to receive an optical disk 642. Also included are a mouse 646 (or other point-and-click device, coupled to bus 612 via serial port 628), a modem 647 (coupled to bus 612 via serial port 630), and a network interface 648 (coupled directly to bus 612).

Bus 612 allows data communication between central processor 614 and system memory 617, which may include read-only memory (ROM) or flash memory (neither shown), and random access memory (RAM) (not shown), as previously noted. The RAM is generally the main memory into which the operating system and application programs are loaded. The ROM or flash memory can contain, among other code, the Basic Input-Output system (BIOS) which controls basic hardware operation such as the interaction with peripheral components or devices. Applications resident with computer system 610 are generally stored on and accessed via a non-transitory computer readable medium, such as a hard disk drive (e.g., fixed disk 644), an optical drive (e.g., optical drive 640), a floppy disk unit 637, or other storage medium. Additionally, applications can be in the form of electronic signals modulated in accordance with the application and data communication technology when accessed via network modem 647 or interface 648.

Storage interface 634, as with the other storage interfaces of computer system 610, can connect to a standard computer readable medium for storage and/or retrieval of information, such as a fixed disk drive 644. Fixed disk drive 644 may be a part of computer system 610 or may be separate and accessed through other interface systems. Modem 647 may provide a direct connection to a remote server via a telephone link or to the Internet via an internet service provider (ISP). Network interface 648 may provide a direct connection to a remote server via a direct network link to the Internet via a POP (point of presence). Network interface 648 may provide such connection using wireless techniques, including digital cellular telephone connection, Cellular Digital Packet Data (CDPD) connection, digital satellite data connection or the like.

Many other devices or subsystems (not shown) may be connected in a similar manner (e.g., scanners, digital cameras and so on). Conversely, all of the devices shown in FIG. 6 need not be present to practice the present systems and methods. The devices and subsystems can be interconnected in different ways from that shown in FIG. 6. The operation of a computer system such as that shown in FIG. 6 is readily known in the art and is not discussed in detail in this application. Code to implement the present disclosure can be stored in a non-transitory computer-readable medium such as one or more of system memory 617, fixed disk 644, optical disk 642, or floppy disk 638. The operating system provided on computer system 610 may be MS-DOS®, MS-WINDOWS®, OS/2®, UNIX®, Linux®, or another known operating system.

Moreover, regarding the signals described herein, those skilled in the art will recognize that a signal can be directly transmitted from a first block to a second block, or a signal can be modified (e.g., amplified, attenuated, delayed, latched, buffered, inverted, filtered, or otherwise modified) between the blocks. Although the signals of the above described embodiment are characterized as transmitted from one block to the next, other embodiments of the present systems and methods may include modified signals in place of such directly transmitted signals as long as the informational and/or functional aspect of the signal is transmitted between blocks. To some extent, a signal input at a second block can be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

INDUSTRIAL APPLICABILITY

In general, embodiments of the present disclosure relate to exercise systems, devices, and methods that enable an exerciser to take an outdoor exercise experience indoors and/or an indoor exercise experience outdoors. Taking an outdoor exercise experience indoors can be done by tracking various parameters and data regarding an outdoor exercise performed by an exerciser. The tracked parameters and date can be used to create an exercise program for an indoor exercise device. The exercise program can cause the exercise device to simulate the outdoor exercise. For instance, the exercise program can cause the exercise device to adjust its operating parameters (e.g., incline, decline, tilt, speed) to simulate the parameters of the outdoor exercise experience (e.g., the terrain of the outdoor route, the exerciser's outdoor speed).

Taking the outdoor exercise experience indoors can be particularly useful when outdoor conditions (e.g., weather, construction) or an exerciser's schedule prevents the exerciser from exercising outdoors. For instance, if an exerciser typically runs a particular outdoor route each morning before work, the exerciser can use the disclosed exercise system to create an exercise program that will simulate that route on the exerciser's indoor exercise device. Thus, on bad weather mornings, the exerciser can run a simulated version of his/her normal route without having to go outside.

Additionally, groups of exercisers can use the disclosed exercise system. By way of example, the disclosed exercise system may be employed by a group of friends that regularly run a particular route together. The group of runners could use the disclosed exercise system to take their regular run indoors. For instance, one or more of the runners could carry an exercise monitoring device with them when running the group's regular route. The exercise monitoring device may gather data about the route (e.g., GPS data, images, elevation changes, distance, incline, decline). An exercise program that simulates the group's regular route can be created using the data gathered with the exercise monitoring device.

Each member of the group may access/retrieve the program from a remote communication system and run the exercise program on their own exercise device. Thus, when there is inclement weather or other conditions that prevent the group from running together outdoors, the members of the groups can run a simulation of their regular route indoors. As with an individual exerciser, the exercise system can monitor the performances of each of the group members as they exercise on their exercise devices. Data regarding the group members' performances can be uploaded to the remote communication system for analysis and comparison.

When the members of the group have identified themselves at the remote communication system as being part of a group, the remote communication system may compare the group members' performances to one another. For instance, if the remote communication system receives performance information about multiple members of the group, the remote communication system may determine whether each member performed the same simulated route program and when. If the members performed the same exercise program and the start times for the members are within a predetermined window of time (e.g., within two hours of each other), the remote communication system may compare the performances of the group members. The comparison may determine a winner of a race conducted between the group members on their exercise devices. The comparison may also determine who burned the most calories, etc.

Additionally, the remote communication system may allow exerciser's to annotate their performance information for each exercise routine. For instance, an exerciser may create notes associated with a particular exercise routine that indicates who the exerciser ran with that day, how the exerciser felt about his/her performance, or other information that may help the exerciser to remember and distinguish one exercise routine from another.

In addition to groups sharing programs that simulate regular routes run by the groups, exercisers may share programs of routes they have created or run. For instance, an exerciser may have an exercise program created based upon a route he/she ran. The exerciser may then share that exercise program with his/her friends via the remote communication system. For example, an exerciser may run a route while on vacation and have an exercise program made to simulate the route. The exerciser may share this exercise program with his/her friends so that they can have the same, albeit simulated, experience that their friend had.

In addition to taking outdoor exercise experiences indoors, the disclosed exercise system also allows exercisers to take indoor exercise experiences outdoors. For instance, an exerciser may run an exercise program on his/her indoor exercise device that simulates an outdoor route. The route may be predefined or it may be user defined. In either case, the exerciser's performance may be monitored as the exerciser runs the simulated route. The exerciser can then go outdoors and run the actual outdoor route. As the exerciser runs the actual outdoor route, the exercise system (typically via an exercise monitoring device) can track the exerciser's performance and compare it to the exerciser's indoor performance for the same route.

The indoor-to-outdoor component of the exercise system can be particularly useful in training. For instance, an exercising may be planning on running in an upcoming race that has a course that would be difficult to regularly run outdoors (due to location, traffic, etc.). Nevertheless, the exerciser may still wish to train on the race course. Accordingly, the exerciser could use the disclosed exercise system to create or obtain an exercise program that will simulate the race course on the exerciser's indoor exercise device. As a result, the exerciser can train for the upcoming race without having to actually run the race course on a regular basis.

Nevertheless, the exercise system does enable the exerciser to run the actual race course and compare his/her performance to previous indoor performances. For instance, as the exerciser runs the actual race course, the exercise system (typically through the exercise monitoring device) may provide prompts to the exerciser to inform the exerciser how the current performance compares to past indoor performances and/or goals set by the exerciser.

While embodiments of the invention have been described in the context of a motorized treadmill, it is understood that the invention is not limited to any particular type of exercise device. Accordingly, the term "exercise device" shall refer broadly to any type of device that takes the form of an exercise machine, including, but not limited to, treadmills, exercise cycles, Nordic style ski exercise devices, rowers, steppers, hikers, climbers, and elliptical or striding exercise devices. These various types of exercise devices may include adjustable operating parameters similar to those described above (e.g., speed, incline, etc.). Additionally, these exercise devices may also have adjustable operating parameters such as resistance to the movement of a movable element (e.g., belt, pedal, link arm, etc.).

What is claimed is:

1. An exercise system comprising:
   an exercise monitoring device that gathers data regarding an outdoor exercise routine;
   a remote communication system communicatively connectable to the exercise monitoring device, the remote communication system being receptive to the data regarding the outdoor exercise routine, wherein the remote communication system generates an exercise program based on the data regarding the outdoor exercise routine, the exercise program includes one or more images of the outdoor exercise routine synchronized with one or more control commands to an exercise device; and
   the exercise device is communicatively connectable to the remote communication system, the exercise device being receptive to the exercise program, wherein the exercise program causes the exercise device to simulate one or more aspects of the outdoor exercise routine.

2. The exercise system of claim 1, wherein the exercise monitoring device comprises one or more sensors that gather data about the outdoor exercise routine, including at least one of GPS data, distance traveled, elevation, elevation changes, time duration, incline, and decline.

3. The exercise system of claim 1, wherein the exercise monitoring device comprises at least one of a display and a speaker.

4. The exercise system of claim 1, wherein the remote communication system generates the exercise program by the creating one or more control commands that cause adjustments to one or more operating parameters of the exercise device.

5. The exercise system of claim 4, wherein the adjustments to the one or more operating parameters simulate the one or more aspects of the outdoor exercise routine.

6. The exercise system of claim 5, wherein the one or more simulated aspects of the outdoor exercise routine include at least one of incline, decline, and speed.

7. The exercise system of claim 1, wherein simulation of the one or more aspects of the outdoor exercise routine comprises presenting the one or more images of the outdoor exercise routine on a display of the exercise device.

8. An exercise system comprising:
   a remote communication system that generates an exercise program based on data regarding an outdoor exercise route, the exercise program comprising (i) control commands representative of terrain of the outdoor exercise route and (ii) images of the outdoor exercise route that are synchronized with the control commands;
   an exercise device communicatively connected to the remote communication system, the exercise device being receptive to the exercise program, wherein the exercise device simulates the outdoor exercise route in response to the exercise program, wherein data regarding an exerciser's performance of the simulated exercise route is gathered during the performance of the simulated exercise route; and
   an exercise monitoring device that gathers data regarding an exerciser's performance of an exercise performed along the outdoor exercise route and compares that data to the data regarding the exerciser's performance of the simulated exercise route.

9. The exercise system of claim 8, wherein the exercise monitoring device provides prompts to the exerciser while the exerciser performs the exercise along the outdoor exercise route.

10. The exercise system of claim 9, wherein the prompts inform the exercise about the exerciser's performance along the outdoor exercise route in comparison to the exerciser's performance of the simulated exercise route.

11. An exercise system comprising:
    an exercise monitoring device that gathers data regarding an outdoor exercise routine;
    a remote communication system communicatively connectable to the exercise monitoring device, the remote communication system being receptive to the data regarding the outdoor exercise routine; and
    an exercise device that is communicatively connectable to the remote communication system, the exercise device being receptive to the data regarding the outdoor exercise routine, wherein the exercise device generates an exercise program based on the data regarding the outdoor exercise routine exercise program, wherein the exercise program causes the exercise device to simulate one or more aspects of the outdoor exercise routine; and
    the exercise device generates the exercise program by synchronizing one or more images of the outdoor exercise routine with one or more control commands of the exercise program.

12. The exercise system of claim 11, wherein the exercise monitoring device comprises one or more sensors that gather data about the outdoor exercise routine, including at least one of GPS data, distance traveled, elevation, elevation changes, time duration, incline, and decline.

13. The exercise system of claim 11, wherein the exercise monitoring device comprises at least one of a display and a speaker.

14. The exercise system of claim 11, wherein the exercise device generates the exercise program by creating the one or more control commands that cause adjustments to one or more operating parameters of the exercise device.

15. The exercise system of claim 14, wherein the adjustments to the one or more operating parameters simulate the one or more aspects of the outdoor exercise routine.

16. The exercise system of claim 15, wherein the one or more simulated aspects of the outdoor exercise routine include at least one of an incline, a decline, and a speed.

17. The exercise system of claim 11, wherein simulation of the one or more aspects of the outdoor exercise routine comprises presenting the one or more images of the outdoor exercise routine on a display of the exercise device.

* * * * *